(12) United States Patent
Lee et al.

(10) Patent No.: US 9,018,184 B2
(45) Date of Patent: Apr. 28, 2015

(54) INHIBITORS OF SP140 AND THEIR USE IN THERAPY

(75) Inventors: Kevin Lee, Stevenage (GB); David Francis Tough, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/883,091

(22) PCT Filed: Nov. 23, 2011

(86) PCT No.: PCT/EP2011/070781
§ 371 (c)(1),
(2), (4) Date: May 2, 2013

(87) PCT Pub. No.: WO2012/069525
PCT Pub. Date: May 31, 2012

(65) Prior Publication Data
US 2013/0225661 A1    Aug. 29, 2013

(30) Foreign Application Priority Data

Nov. 25, 2010    (GB) .................................. 1020015.2

(51) Int. Cl.
*C12N 15/11* (2006.01)
*C12Q 1/68* (2006.01)
*A61K 31/713* (2006.01)
*C12N 15/113* (2010.01)

(52) U.S. Cl.
CPC ............ *A61K 31/713* (2013.01); *C12N 15/113* (2013.01); *C12N 2310/14* (2013.01); *C12Q 1/6876* (2013.01)

(58) Field of Classification Search
CPC ........... C12Q 2600/158; C12Q 1/6883; C12N 15/113; C12N 2310/14; A61K 38/00
See application file for complete search history.

(56) References Cited

U.S. PATENT DOCUMENTS

2003/0216548 A1    11/2003    Bloch et al.

FOREIGN PATENT DOCUMENTS

WO    WO2011054843    5/2012

OTHER PUBLICATIONS

Bloch et al, Identification and Characterization of a Leukocyte-Specific Component of the Nuclear Body, 1996, Journal of Biological Chemistry, vol. 271, 46: 29198-29204.*
Aigner, Gene silencing through RNA interference (RNAi) in vivo: Strategies based on the direct application of siRNAs, 2006, Journal of Biotechnology, 124: 12-25.*
Bloch, D.B., et al. "Identification and Characterization of a Leukocyte-Specific Component of the Nuclear Body." Journal of Biological Chemistry, Nov. 15, 1996, vol. 271(46), pp. 29198-29204.
Granito, A., et al. "PML Nuclear Body Component Sp140 is a Novel Autoantigen in Primary Biliary Cirrhosis." American Journal of Gastroenterology, Jan. 1, 2010, vol. 105(1), pp. 125-131.
Wolters, N.M., et al. "From Sequence to Function: Using RNAi to Elucidate Mechanisms of Human Disease." Cell Death and Differentiation, May 1, 2008, vol. 15(5), pp. 809-819.
Jeanmougin, F., et al. "The Bromodoma in Revisited." Trends in Biochemical Sciences, May 1, 1997, vol. 22(5), pp. 151-153.

* cited by examiner

*Primary Examiner* — Tracy Vivlemore
*Assistant Examiner* — Kate Poliakova
(74) *Attorney, Agent, or Firm* — Robert H. Brink

(57) ABSTRACT

A method of treating autoimmune and inflammatory diseases or conditions in a mammal, such as a human, which comprises the administration of a inhibitor of bromodomain-containing protein: SP140.

2 Claims, 12 Drawing Sheets

SEQUENCE LISTING

```
<160> NUMBER OF SEQ ID NOS: 11

<210> SEQ ID NO 1
<211> LENGTH: 21
<212> TYPE: DNA
<213> ORGANISM: Human

<400> SEQUENCE: 1
tcgggtgtga tcctaggcca a                                                  21

<210> SEQ ID NO 2
<211> LENGTH: 21
<212> TYPE: DNA
<213> ORGANISM: Human

<400> SEQUENCE: 2
caggatggtc gcagagatcc a                                                  21

<210> SEQ ID NO 3
<211> LENGTH: 21
<212> TYPE: DNA
<213> ORGANISM: Human

<400> SEQUENCE: 3
```

```
caggattaac ctgatggcct a                                              21

<210> SEQ ID NO 4
<211> LENGTH: 21
<212> TYPE: DNA
<213> ORGANISM: Human

<400> SEQUENCE: 4
cccagtgaca agagtgatgt a                                              21

<210> SEQ ID NO 5
<211> LENGTH: 21
<212> TYPE: DNA
<213> ORGANISM: Human

<400> SEQUENCE: 5
aaagggcatt taaacgggaa a                                              21

<210> SEQ ID NO 6
<211> LENGTH: 21
<212> TYPE: DNA
<213> ORGANISM: Human

<400> SEQUENCE: 6
cacctccatg cagaagccct a                                              21

<210> SEQ ID NO 7
<211> LENGTH: 21
<212> TYPE: DNA
<213> ORGANISM: Human

<400> SEQUENCE: 7
ctggtttgcc actgacttca a                                              21

<210> SEQ ID NO 8
<211> LENGTH: 24
<212> TYPE: DNA
<213> ORGANISM: Artificial
<220> FEATURE:
<223> OTHER INFORMATION: TSS_TNFaF

<400> SEQUENCE: 8
gggacatata aaggcagttg ttgg                                           24

<210> SEQ ID NO 9
<211> LENGTH: 22
<212> TYPE: DNA
<213> ORGANISM: Artificial
<220> FEATURE:
<223> OTHER INFORMATION: TSS_TNFaR

<400> SEQUENCE: 9
tccctcttag ctggtcctct gc                                             22

<210> SEQ ID NO 10
<211> LENGTH: 20
<212> TYPE: DNA
<213> ORGANISM: Artificial
<220> FEATURE:
<223> OTHER INFORMATION: 5C_HBBF

<400> SEQUENCE: 10
aacagccaag tcaaatctgc                                                20
```

```
<210> SEQ ID NO 11
<211> LENGTH: 20
<212> TYPE: DNA
<213> ORGANISM: Artificial
<220> FEATURE:
<223> OTHER INFORMATION: 5C_HBBR

<400> SEQUENCE: 11
ggcacacgtg tatccctgag                                              20
```

INHIBITORS OF SP140 AND THEIR USE IN THERAPY

CROSS-REFERENCE TO RELATED APPLICATIONS

This application is filed pursuant to 35 USC 371 as a United States National Phase Application of International Patent Application Serial No. PCT/EP2011/070781 filed on Nov. 23, 2011, which claims priority from 1020015.2 filed on Nov. 25, 2010 in the United Kingdom.

FIELD OF THE INVENTION

The present invention is concerned with new methods of treatment. More particularly, the present invention relates to methods for treatment or prevention of autoimmune and inflammatory diseases and conditions by inhibiting or modifying the expression or function of bromodomain-containing proteins. In a further aspect the invention relates to a method for identifying agents useful in said methods of treatment. The invention particularly describes the role of certain bromodomain—containing proteins, particularly SP140 in these diseases and conditions and their use as therapeutic and screening targets.

BACKGROUND OF THE INVENTION

Chromatin is the complex combination of DNA and protein that makes up chromosomes. It is found inside the nuclei of eukaryotic cells and is divided between heterochromatin (condensed) and euchromatin (extended) forms. A range of different states of condensation are possible and the tightness of this structure varies during the cell cycle, being the most compact during the process of cell division. The major components of chromatin are DNA and proteins. Histones are the chief protein components of chromatin, acting as spools around which DNA winds. The basic building blocks of chromatin are nucleosomes, each of which is composed of 146 base pairs of DNA wrapped around a histone octamer that consists of 2 copies of each H2A, H2B, H3 and H4. The functions of chromatin are to package DNA into a smaller volume to fit in the cell, to strengthen the DNA to allow mitosis and meiosis, and to serve as a mechanism to control expression and DNA replication. Chromatin contains genetic material serving as instructions to direct cell functions. The genomes of eukaryotic organisms are highly organised within the nucleus of the cell. The chromatin structure is controlled by a series of post translational modifications to histone proteins, notably histones H3 and H4, and most commonly within the "histone tails" which extend beyond the core nucleosome structure. Histone tails tend to be free for protein—protein interaction and are also the portion of the histone most prone to post-translational modification. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Lysine acetylation is a histone modification that forms an epigenetic mark on chromatin for bromodomain-containing proteins to dock and in turn, regulate gene expression. Distinct classes of enzymes, namely histone acetyltransferases (HATs) and histone deacetylases (HDACs), acetylate or de-acetylate specific histone lysine residues (1).

The bromodomain is currently the only protein domain known to specifically bind to acetylated lysine residues in histone tails. Bromodomains, which are approximately 110 amino acids long, are found in a large number of chromatin-associated proteins and have now been identified in approximately 70 human proteins, often adjacent to other protein motifs (2,3). Proteins that contain a bromodomain may contain additional bromodomains, as well as other functional motifs. For example, many HATs also contain a bromodomain (2). Interactions between bromodomains and modified histones may be an important mechanism underlying chromatin structural changes and gene regulation. Bromodomain-containing proteins have been implicated in disease processes including cancer, inflammation and viral replication. The development of inhibitors to bromodomains is thus an attractive means for controlling gene expression, and there is a need in the art to regulate bromodomain binding to acetylated lysine in order to control gene expression.

The present inventors have identified bromodomain-containing proteins involved in the inflammatory response. Inhibiting these bromodomain-containing proteins by inhibiting expression and/or function therefore would provide a novel approach to the treatment of autoimmune and inflammatory diseases or conditions.

SUMMARY OF THE INVENTION

Thus in one aspect there is provided a method of treating autoimmune and inflammatory diseases and conditions which comprises inhibiting one or more bromodomain-containing proteins in a mammal.

In a further aspect there is provided a method of treatment of autoimmune and inflammatory diseases and conditions in a mammal comprising administering a therapeutically effective amount of an inhibitor of SP140.

In a further aspect there is provided the use of a bromodomain-containing protein inhibitor in the manufacture of a medicament for the treatment of autoimmune and inflammatory diseases and conditions in a mammal.

In a further aspect the present invention provides the use of an inhibitor of SP140 in the manufacture of a medicament for the treatment of autoimmune and inflammatory diseases and conditions.

In a further aspect the present invention provides an inhibitor of the bromodomain-containing protein SP140 for use in the treatment of autoirnmune and inflammatory diseases and conditions o.

In a further aspect there is provided a pharmaceutical formulation for use in the treatment of autoimmune and inflammatory diseases or conditions, comprising an inhibitor of the bromodomain-containing protein SP140, together with at least one pharmaceutical carrier.

In a further aspect, there is provided a method of screening for an inhibitor of the bromodomain-containing protein SP140, in particular comprising the step of determining whether the compound inhibits or the step of determining whether the compound activates the bromodomain-containing protein SP140.

DETAILED DESCRIPTION OF THE INVENTION

Figure 1:
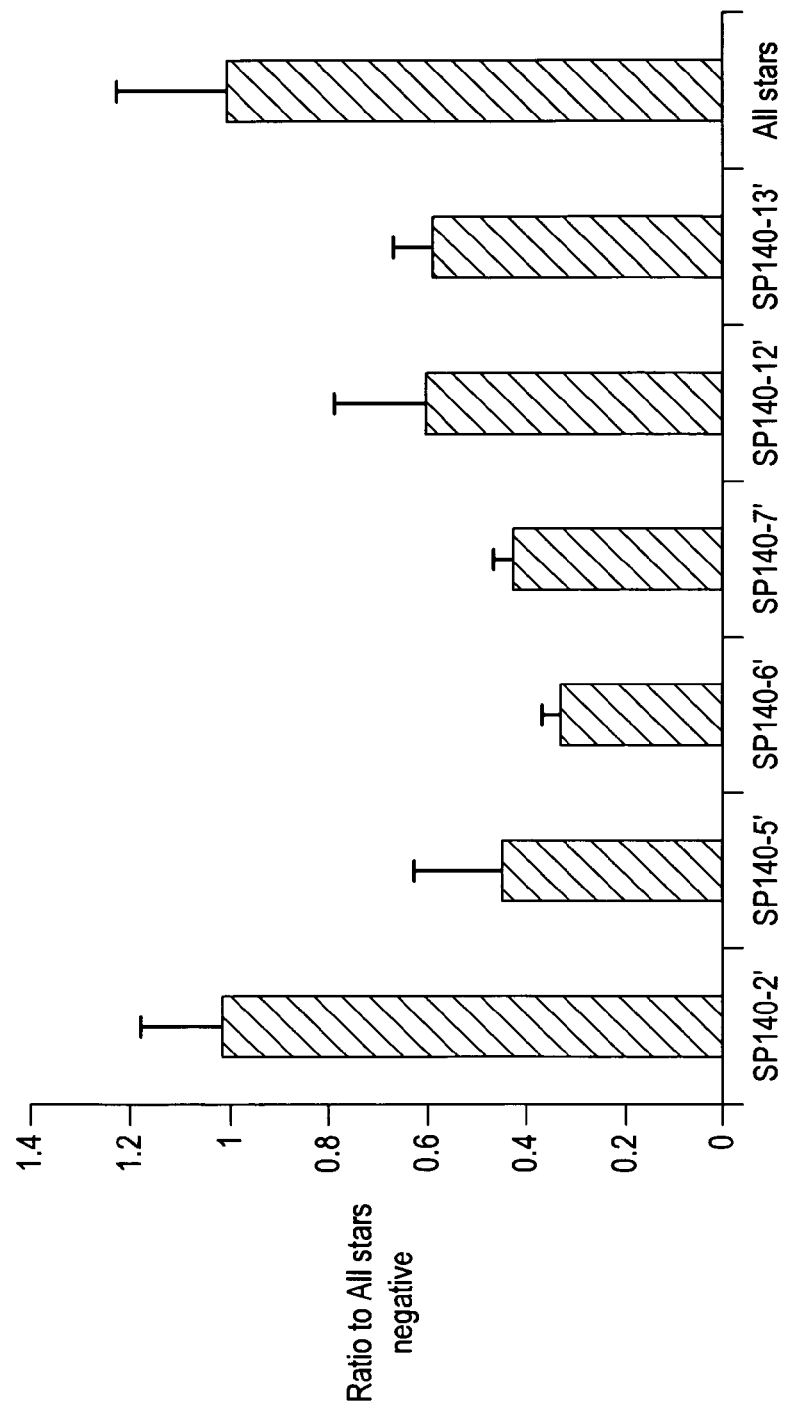
FIG. 1. siRNAs targeting SP140 reduce levels of SP140 mRNA in primary human CD4$^+$ T cells. Six different siRNAs designed to target SP140 were tested for their ability to reduce SP140 mRNA levels after transfection into primary human CD4+ T cells. SP140 mRNA levels were quantified by RT-PCR 24 hours after transfection with SP140 siRNA or scrambled non-targeting control siRNA (termed All stars). SP140 mRNA amounts were normalised to GAPDH and the results are plotted as fractions of the quantity detected in cells transfected with the All stars siRNA.

Various bromodomain-containing proteins have been identified and characterised. The following is particularly mentioned:

SP140:

The nucleic acid sequence of human SP140 mRNA, including transcript variants, is provided by the following accession numbers: NM_007237.4, NM_001005176.2. The amino acid sequence of human SP140 protein, including isoforms, is provided by the following accession numbers: NP_009168.4, NP_001005176.1.

Within the scope of the present invention, an inhibitor of a human bromodomain-containing protein is preferably used, more particularly an inhibitor of SP140 particularly an inhibitor compound.

As used herein the term "polypeptide" refers to an amino acid chain including a full-length protein, oligopeptides, short peptides and fragments thereof, wherein the amino acid residues are linked by covalent bonds.

As used herein a "variant" is a polypeptide comprising a sequence, which differs (by deletion of an amino acid, insertion of an amino acid, and/or substitution of an amino acid for a different amino acid) in one or more amino acid positions from that of a parent polypeptide sequence. The variant sequence may be a non-naturally occurring sequence, i.e. a sequence not found in nature.

As used herein the term "synthetic peptide" refers to a peptide, including a short peptide that has been synthesized in vitro. The term further encompasses peptides or short peptides that have been modified by substitution with unusual or non-natural amino acids.

As used herein "naturally occurring" as applied to an object refers to the fact that the object can be found in nature as distinct from being artificially produced by man.

As used here in a "fragment" or "subsequence" refers to any portion of a given sequence. It is to be understood that a fragment or subsequence of a sequence will be shorter than the sequence itself by at least one amino acid or one nucleic acid residue. Thus, a fragment or subsequence refers to a sequence of amino acids or nucleic acids that comprises a part of a longer sequence of amino acids (e.g. polypeptide).

As used herein the term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of polypeptide sequences or nucleotide sequences.

As used herein the term "nucleic acid molecule" refers to an oligomer or polymer of ribonucleic acid (RNA) or deoxyribonucleic acid (DNA) or mimetics thereof. This term includes molecules composed of naturally-occurring nucleobases, sugars and covalent internucleoside (backside) linkages which function similarly or combinations thereof.

As used herein a "polynucleotide sequence" (e.g. a nucleic acid, polynucleotide, oligonucleotide, etc.) is a polymer of nucleotides comprising nucleotides A,C,T,U,G, or other naturally occurring nucleotides or artificial nucleotide analogues, or a character string representing a nucleic acid, depending on context. Either the given nucleic acid or the complementary nucleic acid can be determined from any specified polynucleotide sequence.

As used herein, the term "inhibitor" can be any compound or treatment capable of inhibiting the expression and/or function of the bromodomain- containing protein, i.e. any compound or treatment that inhibits transcription of the gene, RNA maturation, RNA translation, post-translational modification of the protein, binding of the protein to an acetylated lysine target and the like. Thus "inhibiting the bromodomain-containing protein SP140" includes inhibiting the expression and/or function of the bromodomain-protein SP140.

The inhibitor may be of varied nature and origin including natural origin [e.g. plant, animal, eukaryotic, bacterial, viral] or synthetic [particularly an organic, inorganic, synthetic or semi-synthetic molecule]. For example it can be a nucleic acid, a polypeptide, a protein, a peptide or a chemical compound. In one aspect the inhibitor is selective for a particular bromodomain—containing protein with no activity against other bromodomains—containing protein.

In one aspect the inhibitor is an antisense nucleic acid capable of inhibiting transcription of the bromodomain—containing proteins or translation of the corresponding messenger RNA. The antisense nucleic acid can comprise all or part of the sequence of the bromodomain-containing protein, or of a sequence that is complementary thereto. The antisense sequence can be a DNA, and RNA (e.g. siRNA), a ribozyme, etc. It may be single-stranded or double stranded. It can also be a RNA encoded by an antisense gene. When an antisense nucleic acid comprising part of the sequence of the gene or messenger RNA under consideration is being used, it is preferred to use a part comprising at least 10 consecutive bases from the sequence, more preferably at least 15, in order to ensure specific hybridisation. In the case of an antisense oligonucleotide, it typically comprises less than 100 bases, for example in the order of 10 to 50 bases. This oligonucleotide can be modified to improve its stability, its nuclease resistance, its cell penetration, etc. Perfect complementarily between the sequence of the antisense molecule and that of the target gene or messenger RNA is not required, but is generally preferred.

According to another embodiment, the inhibitor compound is a polypeptide. It may be, for example a peptide comprising a region of the bromodomain—containing protein, and capable of antagonising its activity. A peptide advantageously comprises from 5 to 50 consecutive amino acids of the primary sequence of the bromodomain—containing protein under consideration, typically from 7 to 40. The polypeptide can also be an antibody against the bromodomain-containing protein, or a fragment or derivative of such an antibody, for example a Fab fragment, a CDR region, or, more preferably, a single chain antibody (e.g. ScFv). Single chain antibodies are particularly advantageous insofar as they can act in a specific and intracellular fashion to modulate the activity of a target protein. Such antibodies, fragments, or derivatives can be produced by conventional techniques comprising immunising an animal and recovering the serum (polyclonal) or spleen cells (in order to produce hybridomas by fusion with appropriate cell lines).

Methods for producing polyclonal antibodies in various species are described in the prior art. Typically, the antigen is combined with an adjuvant (e.g. Freund's adjuvant) and administered to an animal, typically by subcutaneous injection. Repeated injections can be performed. Blood samples are collected and the immunoglobulin or serum is separated. Conventional methods for producing monoclonal antibodies comprise immunising of an animal with an antigen, followed by recovery of spleen cells, which are then fused with immortalised cells, such as myeloma cells. The resulting hybridomas produce monoclonal antibodies and can be selected by limiting dilution in order to isolate individual clones. Fab or F(ab')2 fragments can be produced by protease digestion, according to conventional techniques.

According to another embodiment, the inhibitor is a chemical compound, of natural or synthetic origin, particularly an organic or inorganic molecule, capable of modulating the expression or the activity of the bromodomain-containing protein. In a particular embodiment, the inhibitor is a small molecule.

As used herein, the "effective amount" means that amount of a drug or pharmaceutical agent that will elicit the biological or medical response of a tissue, system, animal or human that is being sought, for instance, by a researcher or clinician. Furthermore, the term "therapeutic amount" means any amount which as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. "Therapy" and "treatment" may include treatment and/or prophylaxis.

While it is possible that, for use in therapy, the inhibitor may be administered as the raw chemical, it is possible to present the active ingredient as a pharmaceutical composition. Accordingly, the invention further provides pharmaceutical compositions comprising an agent which inhibits one or more bromodomain-containing proteins, particularly SP140, and one or more pharmaceutically acceptable carriers, diluents, or excipients. The carrier(s), diluents(s) or excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable carriers, diluents or excipients. The pharmaceutical composition can be for use in the treatment and/or prophylaxis of any of the conditions described herein.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by reducing the compound to a suitable fine size and mixing with a similarly prepared pharmaceutical carrier such as an edible carbohydrate, as, for example, starch or mannitol. Flavouring, preservative, dispersing and colouring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions drops, gels or dry powders.

For compositions suitable and/or adapted for inhaled administration, it is preferred that the agent is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction). Compositions adapted for administration by inhalation include the particle dusts or mists. Suitable compositions wherein the carrier is a liquid for administration as a nasal spray or drops include aqueous or oil solutions/suspensions of the active ingredient which may be generated by means of various types of metered dose pressurised aerosols, nebulizers or insufflators.

Aerosol formulations, e.g. for inhaled administration, can comprise a solution or fine suspension of the agent in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the agent, (preferably in particle-size-reduced form, e.g. in micronised form), and optionally a performance modifier such as L-leucine or another amino acid, cellobiose octaacetate and/or metals salts of stearic acid such as magnesium or calcium stearate.

Aerosol formulations are preferably arranged so that each metered dose or "puff" of aerosol contains a particular amount of a compound of the invention. Administration may be once daily or several times daily, for example 2, 3 4 or 8 times, giving for example 1, 2 or 3 doses each time. The overall daily dose and the metered dose delivered by capsules and cartridges in an inhaler or insufflator will generally be double those with aerosol formulations.

Pharmaceutical compositions adapted for vaginal administration may be presented as pessaries, tampons, creams, gels, pastes, foams or spray formulations.

Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

Antisense or RNA interference molecules may be administered to the mammal in need thereof. Alternatively, constructs including the same may be administered. Such molecules and constructs can be used to interfere with the expression of the protein of interest, e.g., the bromodomain-containing protein and as such, modify gene expression. Typically delivery is by means known in the art.

Antisense or RNA interference molecules can be delivered in vitro to cells or in vivo, e.g., to tumors of a mammal. Nodes of delivery can be used without limitations, including: intravenous, intramuscular, intraperitoneal, intra-arterial, local delivery during surgery, endoscopic, subcutaneous, and per os. Vectors can be selected for desirable properties for any particular application. Vectors can be viral or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

The agent may be employed alone or in combination with other therapeutic agents.

The agent for use in the present invention may be used in combination with or include one or more other therapeutic agents and may be administered either sequentially or simultaneously by any convenient route in separate or combined pharmaceutical compositions.

The agent and pharmaceutical compositions contain the invention may be used in combination with or include one or more other therapeutic agents, for example selected from NSAIDS, corticosteroids, COX-2 inhibitors, cytokine inhibitors, anti-TNF agents, inhibitors oncostatin M, anti-malarials, immunsuppressive and cytostatics Methods of Treatment and Diseases Provided herein are methods of treatment or prevention of autoimmune and inflammatory conditions and diseases that can be improved by inhibiting bromodomain-containing proteins and thereby, e.g., modulate the level of expression of acetylation activated and acetylation repressed target genes. A method may comprise administering to a subject, e.g. a subject in need thereof, a therapeutically effective amount of an agent described herein.

Thus in one aspect there is provided the use of a bromodomain inhibitor in the manufacture of a medicament for treating autoimmune and inflammatory diseases or conditions.

In a further aspect there is provided a method of treatment of autoimmune and inflammatory diseases or conditions in a mammal comprising administering a therapeutically effective amount of a bromodomain inhibitor.

In one aspect the bromodomain-containing protein is SP140.

In one aspect the inhibitor inhibits the bromodomain-containing protein SP140.

Based at least on the fact that increased histone acetylation has been found to be associated with inflammation, a method for treating inflammation in a subject may comprise administering to the subject a therapeutically effective amount of one or more agents that decrease acetylation or restore acetylation to its level in corresponding normal cells.

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present and to allow for the physiological process or healing and tissue repair to progress.

The agents may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of the invention include encephalitis, Guillain-Barre syndrome, meningitis, neuromyotonia, narcolepsy, multiple sclerosis, myelitis and schizophrenia.

Examples of inflammation of the vasculature or lymphatic system which may be treated with the compounds of the invention include arthrosclerosis, arthritis, phlebitis, vasculitis, and lymphangitis.

Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The agents may be used to treat autoimmune conditions having an inflammatory component. Such conditions include acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schönlein purpura, Kawasaki's disease, lupus erythematosus, microscopic colitis, microscopic polyarteritis, mixed connective tissue disease, multiple sclerosis, myasthenia gravis, opsocionus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The agents may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated with the agents include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis, chronic pulmonary disease, and inflammation accompanying infectious conditions (e.g., sepsis).

The methods of treatment and uses of the invention can be used in mammals, particularly in humans.

The present invention also provides a method for identifying agents which may be candidate compounds for the treatment of autoimmune and inflammatory diseases or conditions comprising determining whether a compound is capable of inhibiting the bromodomain-containing protein SP140.

Screening Methods

The present invention proposes, for the first time that bromodomain-containing proteins, particularly SP140, are therapeutic targets for the treatment of autoimmune inflammatory diseases and conditions. Thus, the present invention provides new targets for the identification, validation, selection and optimisation of active agents on the basis of their ability to modulate the expression or activity of bromodomain-containing proteins, particularly the bromodomain-containing protein SP140. Such active agents include inhibitors as described above.

The present invention thus pertains to a method of identifying, screening, characterising or defining an agent which is capable of modulating the activity of the bromodomain-containing protein SP140. The methods can be used for screening for example large numbers of candidate compounds for clinical use in inflammatory and autoimmune diseases.

The assays (screening methods) may be performed in a cell-based system, an animal system or by a cell free system. Such techniques will be apparent to a person skilled in the art and may be based on a measure of interaction [e.g. binding, displacement or competition assays) or a measure of a function of activity, transcription and the like.

Thus, for example, the present invention provides a method of testing the ability of an agent to modulate the expression of the bromodomain-containing protein SP140, particularly to inhibit expression. In another example the present invention provides a method of testing the ability of an agent to bind to and optionally modulate the activity of the bromodomain-containing protein SP140, particularly to inhibit activity. In a further example the present invention provides a method for testing the ability of an agent to modulate the activity of the bromodomain-containing protein SP140, particularly to inhibit activity.

Provided herein are screening methods for identifying agents that inhibit bromodomain-containing proteins as being potentially useful in the treatment of prevention of autoimmune and inflammatory diseases and conditions and/or cancer. One method involves screening for an inhibitor of bromodomain—containing protein activity, including the steps of contacting a peptide, which may be modified by acetylation, with a bromodomain, particularly the bromodomain-containing protein SP140 or a fragment thereof in the presence and in the absence of a test substance, and identifying a test substance as an inhibitor or activator of bromodomain activity. Test agents (or substances) for screening as inhibitors of the bromodomain can be from any source known in the art. They can be natural products, purified or mixtures, synthetic compounds, members of compound libraries, etc. The test substances can be selected from those that have been identified previously to have biological or drug activity or from those that have not.

In a further aspect the method of screening for an inhibitor of bromodomain-containing protein includes a binding assay. Thus a compound which inhibits the binding of the bromodomain-containing protein SP140 to its substrate can be identified in competition or direct binding assays. Both direct and competition binding assay formats are similar to the formats used in immunoassays and receptor binding assays and will be generally known to a person skilled in the art.

In one aspect the bromodomain-containing protein is SP140.

Typically the methods use peptides of the SP140 protein. In particular the methods use a human protein. More particularly the protein has the amino acid sequence of human SP140 protein as described in accession number NIP_001420.2. or a fragment thereof or a sequence having at least 75%, 80%, 85%, 90%, 91%, 92%, 93%, 94%, 95%, 96%, 97%, 98% or 99% homology to the amino acid sequence of human SP140 protein or a fragment thereof.

Preferably the fragments are at least 110 amino acids long and include the bromodomain.

The present invention further contemplates analogues of the amino acid sequences formed by conservative amino acid substitution. The principle behind conservative amino acid substitution is that certain amino acid pairs have compatible side chains such that, when one amino acid is substituted for the other, there will be only minimal changes in the tertiary structure of the peptide. Rules for conservative substitutions are explained in Bowie et al. Science 247(1990) 1306-1310. It is an object of the present invention to utilise polypeptides, fragments and variants that retain the ability of the protein to bind substrate. I Where required, each of the polypeptides, fragments and variants, where required, may be provided either in purified or un-purified form, for example as cellular extracts or by purification of the relevant component from such extracts. Alternatively, the polypeptides, fragments and variants can be recombinantly produced by recombinant expression techniques, and purified for use in the assay. Alternatively, the polypeptides, fragments and variants can be expressed recombinantly in a cell for use in cell based assays.

Typically, a polynucleotide encoding the relevant component is provided within an expression vector. Such expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art, such as those described in more detail in the examples of the present application. Promoter sequences may be inducible or constitutive promoters depending on the selected assay format.

As natural substrates for bromodomains have been described to include acetylated histone peptides, preferred substrates could comprise peptides corresponding to these sequences and modifications. Conversely, other peptides with suitable affinity for SP140 could be utilised.

Thus for example the substrate may be a peptide, such a synthetic peptide comprising N-terminal residues of histone 3 or 4, at least 10, 20, 30, 40, 50 or full length. The substrate may be at least 70%, 75%, 80%, 85%, 90%, 91%, 92%, 93%, 94%, 95%, 96%, 97%, 98%, 99%, homologous thereto.

It may be also preferred to use a substrate selected from bulk histones, synthetic peptides and nucleosomes.

The following examples are set forth to illustrate the effectiveness of the approach described in the present invention and to further exemplify particular applications of general processes described above. Accordingly, the following Example section is in no way intended to limit the scope of the invention contemplated herein.

EXAMPLES

To investigate whether SP140 might represent a target for the treatment of autoimmune and inflammatory diseases, we conducted a series of experiments exploring the function of this protein in immune cells. These studies focussed primarily on CD4$^+$ T cells because of their key role in inflammation and autoimmunity. Our initial approach was to assess the functional consequences of reducing SP140 expression using small inhibitory RNA (siRNA). Since a number of disparate factors can influence the whether an siRNA can effectively reduce expression of its target gene, and advanced algorithms capable of accurately predicting efficacious siRNAs have not yet been developed (4), we first tested several siRNAs for their ability to reduce SP140 mRNA levels in human CD4$^+$ T cells (Table 1). As shown in FIG. 1, five of six siRNAs tested were able to reduce SP140 mRNA, while a sixth (SP140-2') demonstrated little or no activity.

TABLE 1

| List of siRNAs used to reduce expression of SP140 | |
|---|---|
| SiRNA name | Sequence |
| SEQID: 1 SP140-2' | TCGGGTGTGATCCTAGGCCAA |
| SEQID: 2 SP140-5' | CAGGATGGTCGCAGAGATCCA |
| SEQID: 3 SP140-6' | CAGGATTAACCTGATGGCCTA |
| SEQID: 4 SP140-7' | CCCAGTGACAAGAGTGATGTA |
| SEQID: 5 SP140-10' | AAAGGGCATTTAAACGGGAAA |
| SEQID: 6 SP140-12' | CACCTCCATGCAGAAGCCCTA |
| SEQID: 7 SP140-13' | CTGGTTTGCCACTGACTTCAA |

The T cells implicated in autoimmunity/inflammation show signs of having been previously activated, exhibiting a memory or effector phenotype. Such cells can be identified and isolated on the basis of the isoform of CD45 that they express, being positive for CD45RO and negative for CD45RA. Therefore, we examined the effect of reducing SP140 expression in human CD45RO$^+$ CD45RA$^-$ memory/effector CD4$^+$ T cells.

siRNAs targeting SP140 were introduced into primary human memory/effector CD4$^+$ T cells isolated from the peripheral blood of healthy donors. These cells were subsequently stimulated with dendritic cells (DCs) derived from unrelated donors. Such DCs express major histocompatability complex (MHC) antigens that are recognised by the T cell receptor (TCR) of the responding T cells. The DCs had also been pre-treated either with LPS or curdlan, two bacterially-derived products that activate the DCs and increase their T cell stimulatory capacity. Since activated DCs are the key cells involved in stimulating T cells in vivo, this protocol is designed to mimic closely the physiological conditions of T cell activation.

Figure 2:
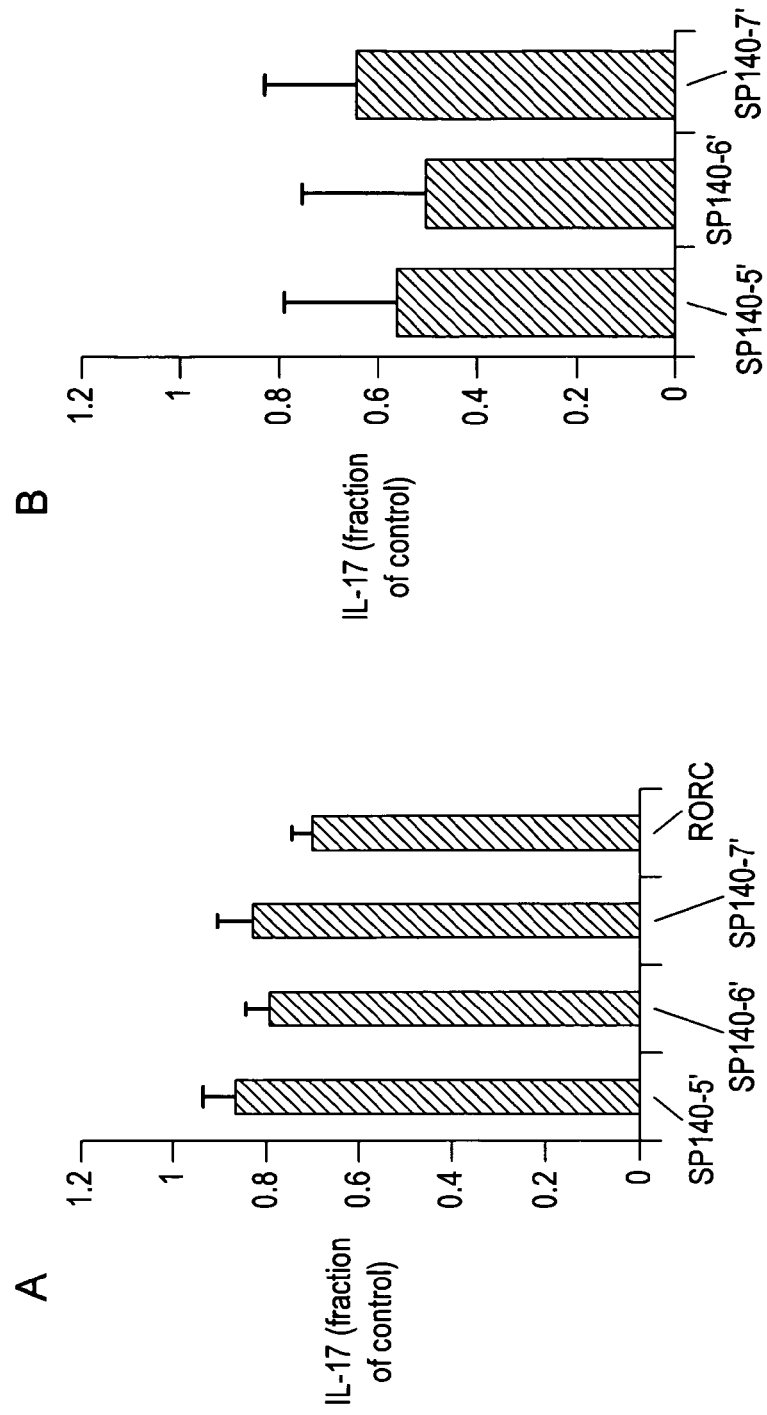
FIG. 2. siRNAs targeting SP140 inhibit IL-17 production by dendritic cell-stimulated human memory/effector CD4+ T cells. CD45RO+ CD45RA+ CD4+ T cells were transfected with 3 different siRNAs targeting SP140 or with a scrambled non-targeting siRNA as a negative control. The siRNA-transfected T cells were stimulated with allogeneic dendritic cells (DCs) that had been activated by (A) curdlan or B (LPS) and cytokines present in the medium 3-4 days later were measured. The results are plotted as the fraction of the amount of IL-17 produced by SP140 siRNA-transfected cells compared to that produced in control siRNA-transfected cells. For curdlan-stimulated DCs, the data represent the mean±SD for 10 donors. For LPS-stimulated DCs, the data represent the mean±SD for 6 separate transfections for each siRNA in DCs from a single donor.
Figure 3:
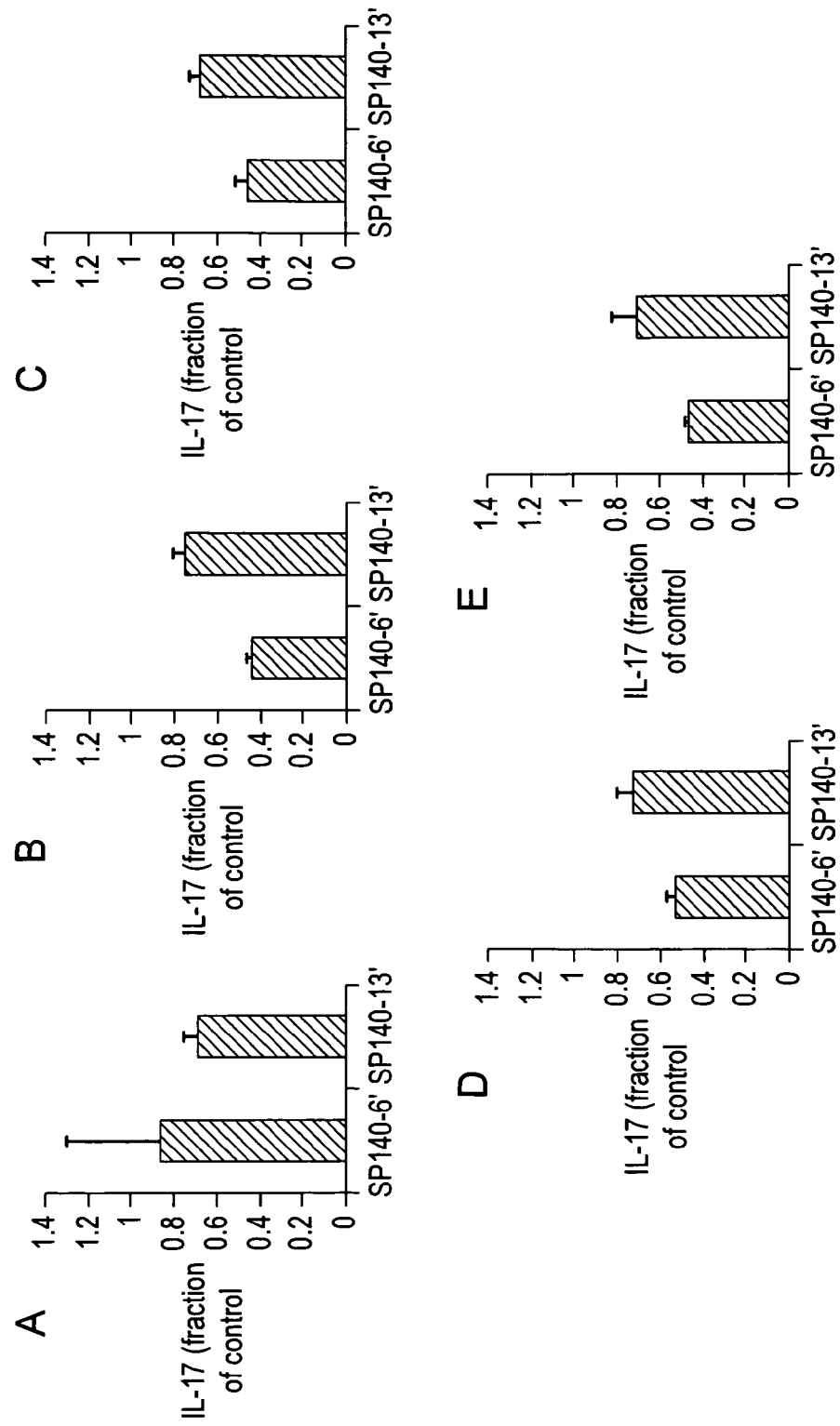
FIG. 3. siRNAs targeting SP140 inhibit cytokine production by anti-CD3+ anti-CD28 -stimulated human memory/effector CD4+ T cells. CD45RO+ CD45RA− CD4+ T cells were transfected with 2 different siRNAs targeting SP140 or with a scrambled non-targeting siRNA as a negative control. Two days after transfection, T cells were added to plates coated with anti-CD3 and anti-CD28 antibodies and cytokines present in the supernatants were measured after a further overnight incubation. The results are plotted as fractions of the amounts of cytokines produced by SP140 siRNA-transfected cells compared to that produced in control siRNA-transfected cells. The data represent the mean±SD for 2 donors.
Figure 4:
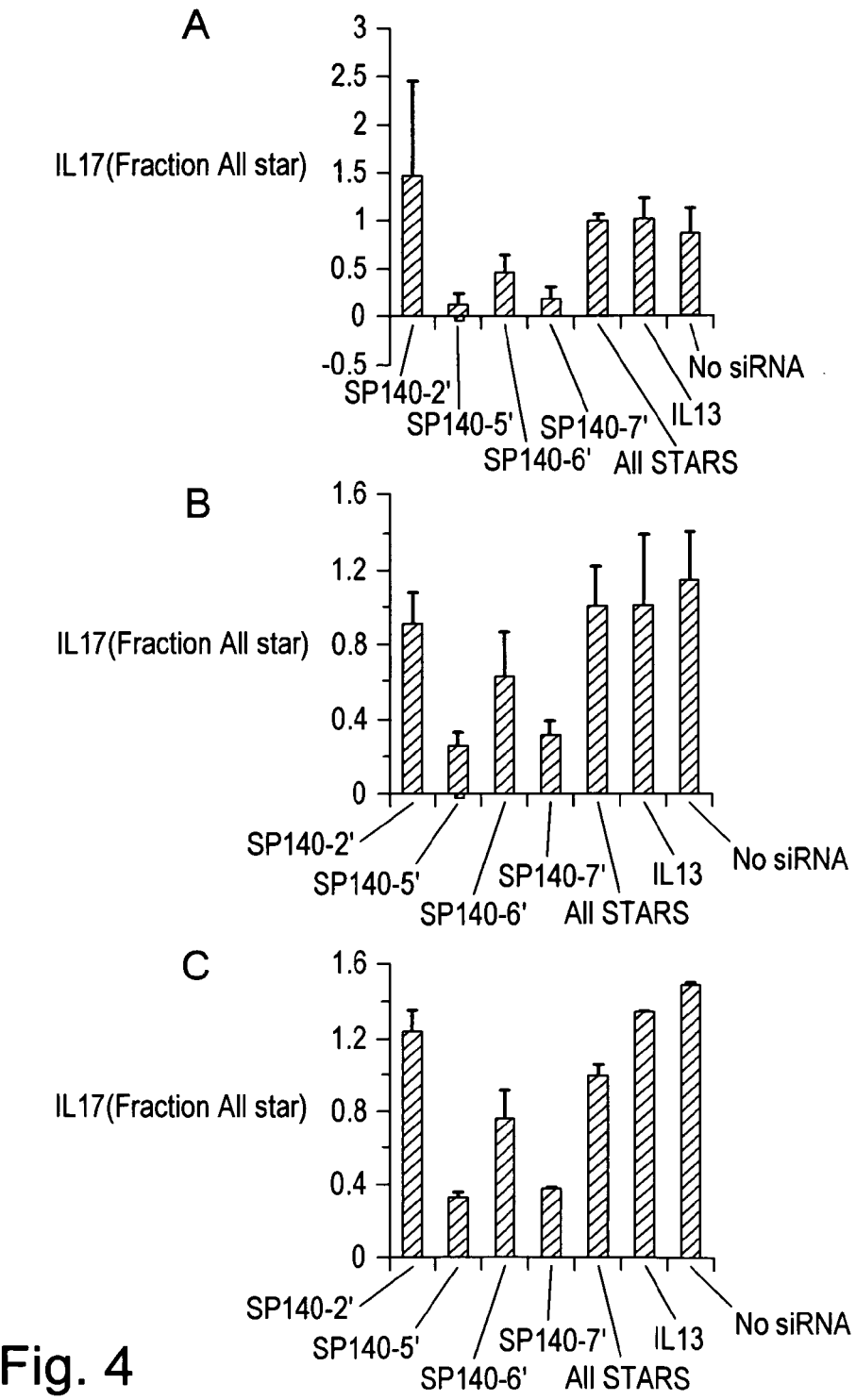
FIG. 4. siRNAs targeting SP140 inhibit cytokine production by an anti-CD3+ anti-CD28 -stimulated human CD4+ T cell line. HuT78 T cells were transfected with 4 different siRNAs targeting SP140 or with a scrambled non-targeting siRNA as a negative control. Two days after transfection, T cells were added to plates coated with anti-CD3 and anti-CD28 antibodies and cytokines present in the supernatants were measured after a further overnight incubation. The results are plotted as fractions of the amounts of cytokines produced by SP140 siRNA-transfected cells compared to that produced in control siRNA-transfected cells. Note that the siRNA designated SP140-2' appears to be ineffective in knocking down SP140 expression (see FIG. 1) and also has little effect on cytokine production. Also, cells were transfected with an siRNA against IL-13, although this proved unsuccessful in knocking down IL-13 expression (C). Data shown are representative of results from two independent experiments.
Figure 4:
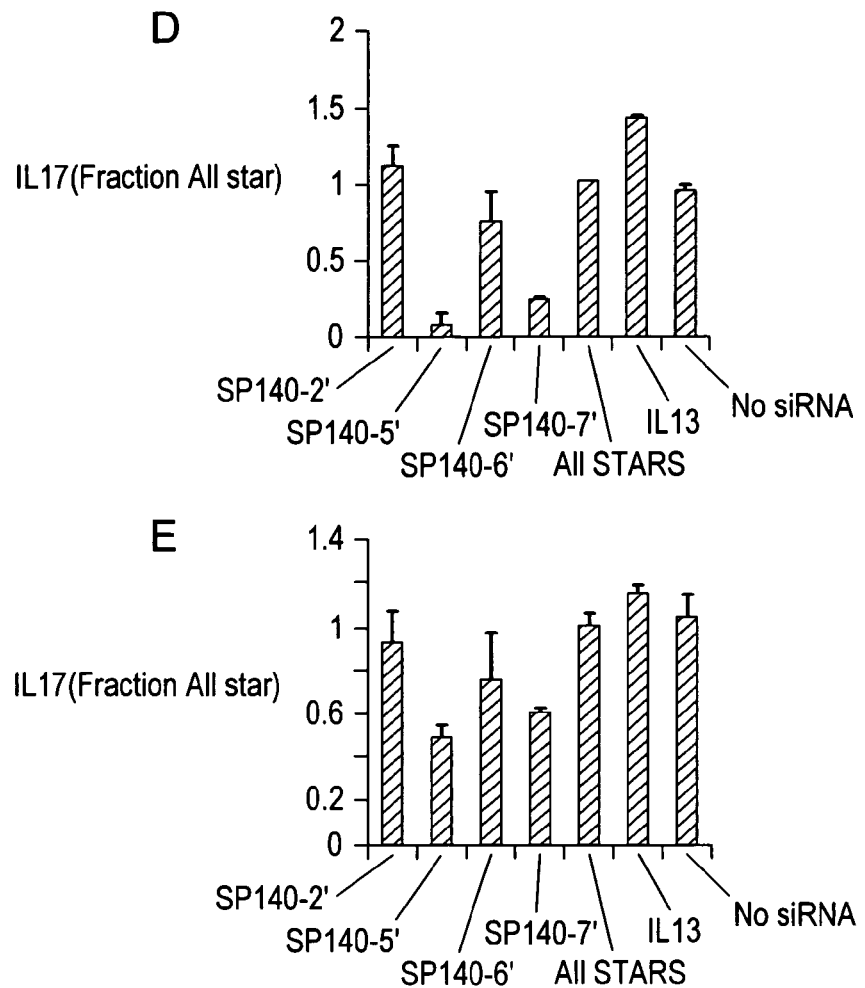

The cytokines present in the medium of the T cell-DC cultures were quantified after 3 days of co-culture. siRNAs directed against the bromodomain-containing protein SP140 were shown to inhibit consistently the production of the pro-inflammatory cytokine IL-17 when introduced into memory/effector $CD4^+$ T cells (FIG. 2). This was evident whether the DCs were activated with curdlan (FIG. 2A) or LPS (FIG. 2B). Given the importance of IL-17 in the promotion of inflammation (5,6), the inhibitory effect of SP140 siRNA on the production of this cytokine results indicated that SP140 contributes to a pro-inflammatory T cell phenotype. In addition to using activated DCs to stimulate T cells, we also examined responses after T cell activation by a combination of anti-CD3 and anti-CD28 antibodies. As shown in FIG. 3, $CD45RO^+$ $CD45RA^-$ $CD4^+$ T cells transfected with siRNAs against SP140 showed reduced production of all of the effector cytokines (IL-17, IFN-γ, IL-13, TNF-α, IL-10) measured after this type of stimulation. Furthermore, similar results were observed when SP140 siRNAs were used to reduce SP140 expression in a human $CD4^+$ T cell line, HuT78 (FIG. 4). As observed after anti-CD3/CD28 stimulation of primary $CD45RO^+$ $CD45RA^-$ $CD4^+$ T cells, HuT78 cells transfected with SP140 siRNAs showed reduced production of all cytokines compared to cells transfected with control siRNA.

Figure 5:
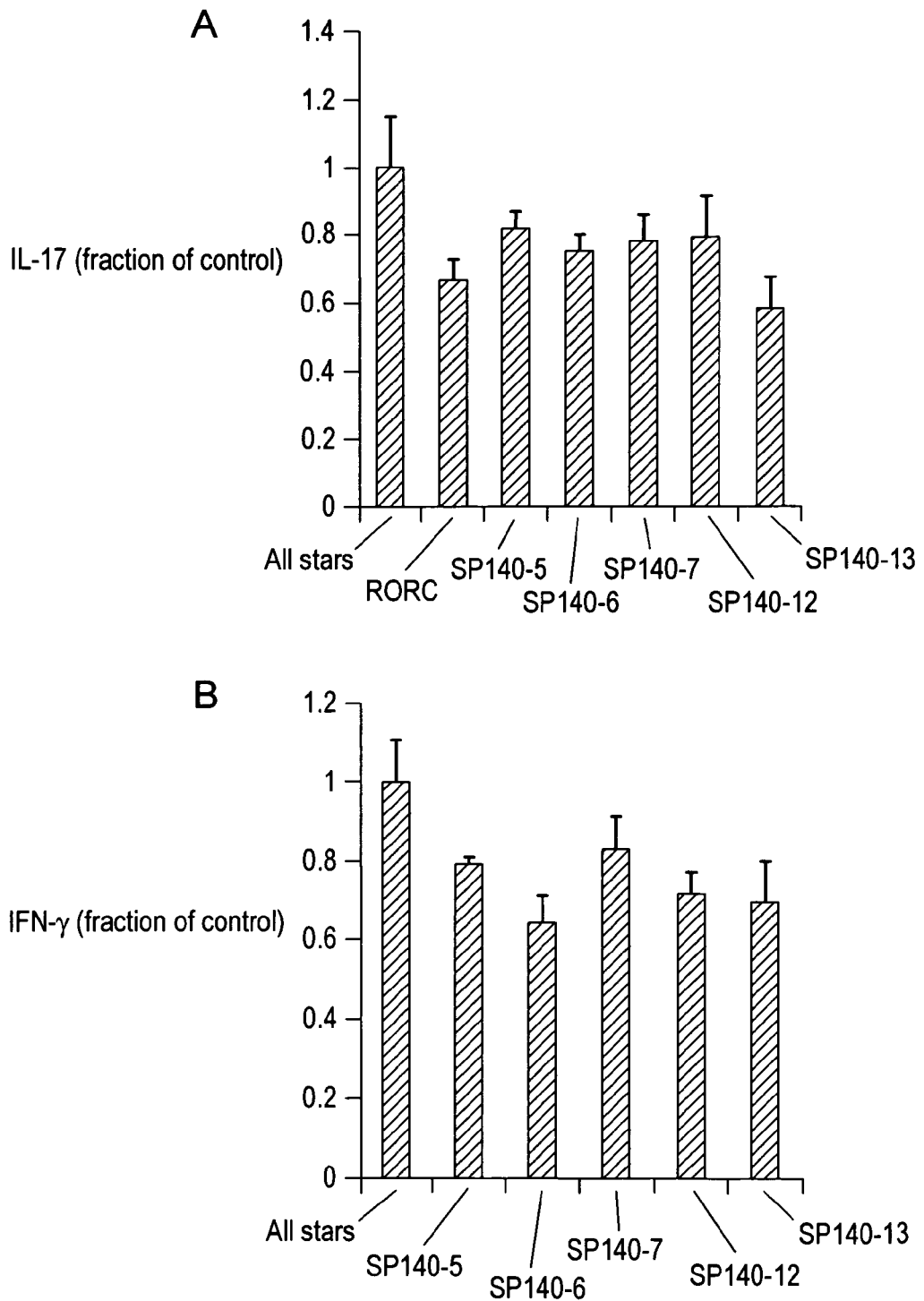
FIG. 5. siRNAs targeting SP140 inhibit cytokine production by anti-CD3+ anti-CD28 -stimulated human CD161+ CD4+ T cells. CD161+ CD4+ T cells isolated from human tonsils were transfected with 5 different siRNAs targeting SP140, with siRNA targeting RORC as a positive control for IL-17 production or with a scrambled non-targeting siRNA as a negative control. Two days after transfection, T cells were added to plates coated with anti-CD3 and anti-CD28 antibodies and cytokines present in the supernatants were measured after a further overnight incubation. The results are plotted as fractions of the amounts of cytokines produced by SP140 siRNA-transfected cells compared to those produced in control siRNA-transfected cells.

Given the importance of IL-17 and IFN-γ in the promotion of autoimmunity and inflammation (5,6), we studied further the role of SP140 in T cells specialised in the production of these cytokines. Specifically, we examined the effect of SP140 siRNAs on the function of $CD161^+$ $CD4^+$ T cells, a T cell subset reported to be specialised in production of IL-17, but which can also produce IFN-γ and is implicated in different types of inflammation (7). As shown in FIG. 5, transfection of SP140 siRNAs into $CD161^+$ $CD45RO^+$ $CD4^+$ T cells prior to stimulation with anti-CD3/CD28 reduced the production of both IL-17 and IFN-γ by these cells. Taken together, these siRNA studies implicate SP140 in the production of pro-inflammatory cytokines by human $CD4^+$ T cells and indicate that approaches to inhibit the expression and/or function of this bromodomain-containing protein would be of benefit for the treatment of autoimmunity and inflammatory diseases and conditions.

Figure 6:
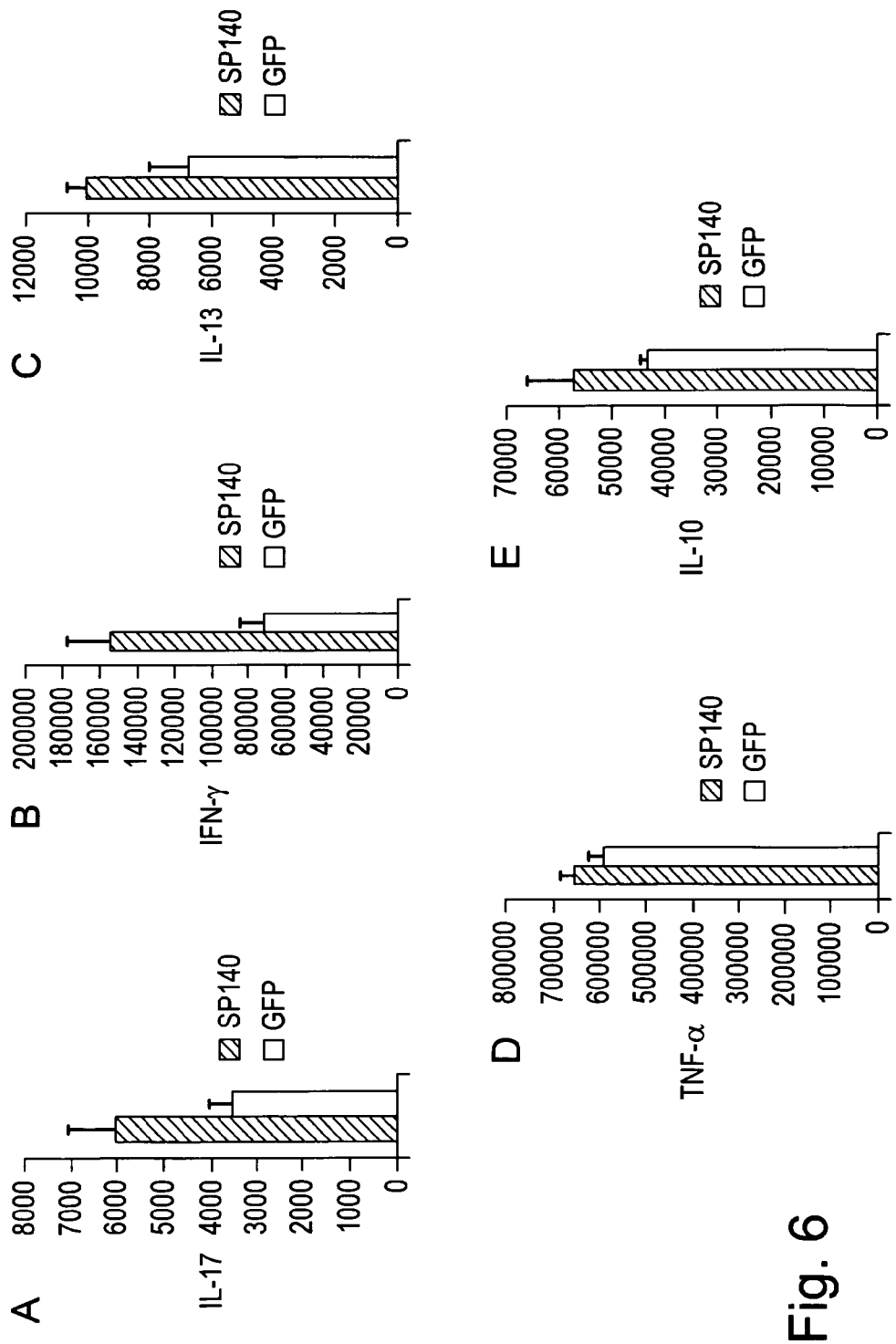
FIG. 6. Overexpression of SP140 in human memory/effector CD4+ T cells enhances cytokine production upon T cell stimulation. Expression plasmids encoding SP140 or green fluorescent protein (GFP) were transfected into human CD45RO+ CD45RA− CD4+ T cells. The transfected T cells were stimulated with allogeneic dendritic cells (DCs) that had been activated by curdlan and cytokines present in the medium 3 days later were measured. The data shown are for one donor representative of three.

As an additional approach to assess the function of SP140 in T cells, we examined the effects of artificially over-expressing SP140 in $CD4^+$ T cells. Plasmids encoding full-length SP140, or green fluorescent protein (GFP) as a control, were transfected into $CD45RO^+$ $CD45RA^-$ $CD4^+$ T cells. The transfected cells were then stimulated with curdlan-activated allogeneic DCs and the cytokines present in the medium three days later were measured. As shown in FIG. 6, cells transfected with the SP140 expression plasmid produced higher levels of IL-17 and IFN-γ than control cells. Taken together with the fact that siRNA treatment yielded the reverse phenotype, these data strongly implicate SP140 in the production of pro-inflammatory cytokines by T cells.

Figure 7:
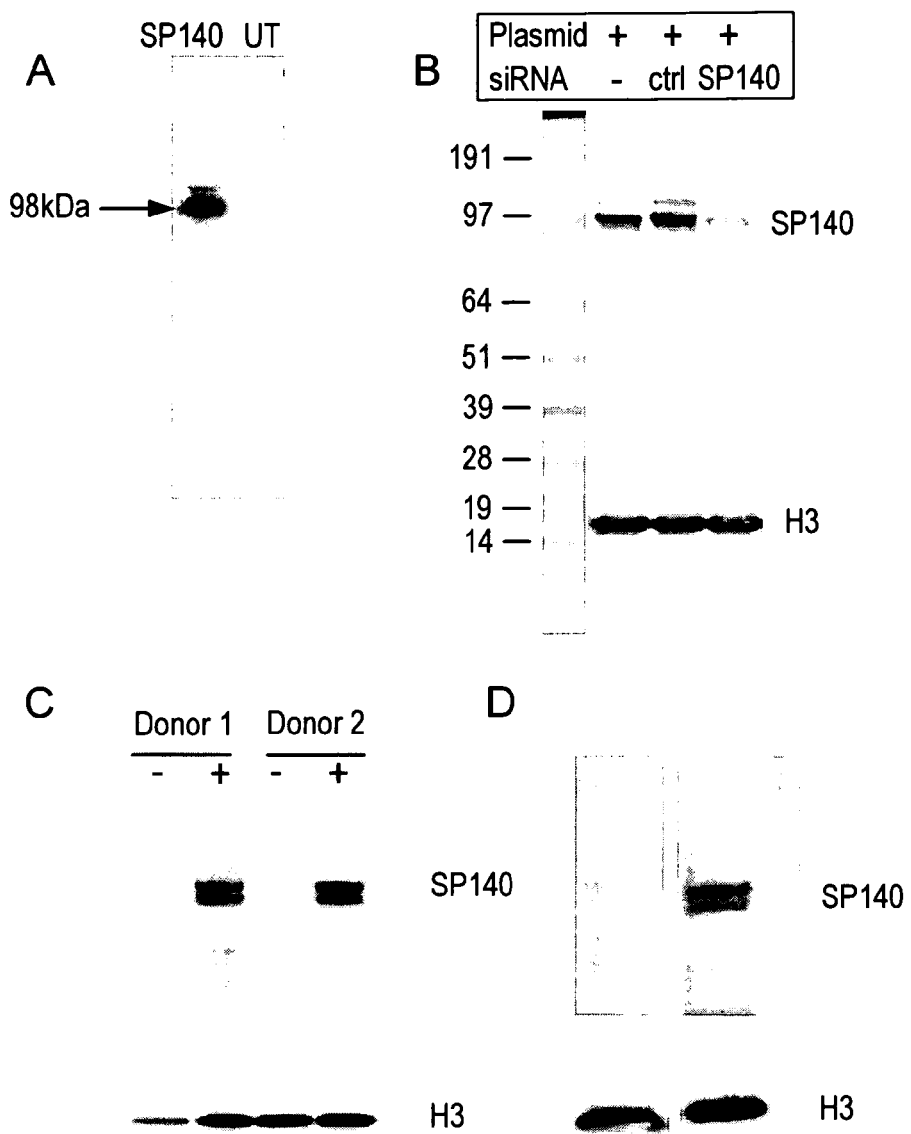
FIG. 7. SP140 protein expression is increased after T or dendritic cell activation. (A, B) Western blots demonstrating specificity of anti-SP140 antibody. (A) Western blot of lysates from untransfected (designated UT) HeLa cells or HeLa cells transfected with a plasmid encoding full-length SP140 (designated SP140) shows a band of the expected molecular weight (98 kDa) only in transfected cells. (B) siRNA targeting SP140 (SP140-6') reduces SP140 expression in HeLa cells transfected with SP140 expression plasmid. Lysates were from cells transfected with the SP140 expression plasmid alone (left lane), with the expression plasmid plus control siRNA (middle lane) or with the expression plasmid plus SP140-6' siRNA (right lane). The blot was probed with an antibody to the control protein histone H3 to compare amount of protein loaded from the different lysates. (C) Increased SP140 protein levels after T cell activation. Monocyte-depleted PBMCs from 2 donors were either left unactivated or treated with anti-CD3+ anti-CD28 antibodies for 24 hours. Lysates were assessed by Western blotting with antibodies to SP140 and histone H3. (D) Increased SP140 protein levels after DC activation. DCs were left unactivated or treated with LPS for 24 hours. Lysates were assessed by Western blotting with antibodies to SP140 and histone H3.
Figure 8:
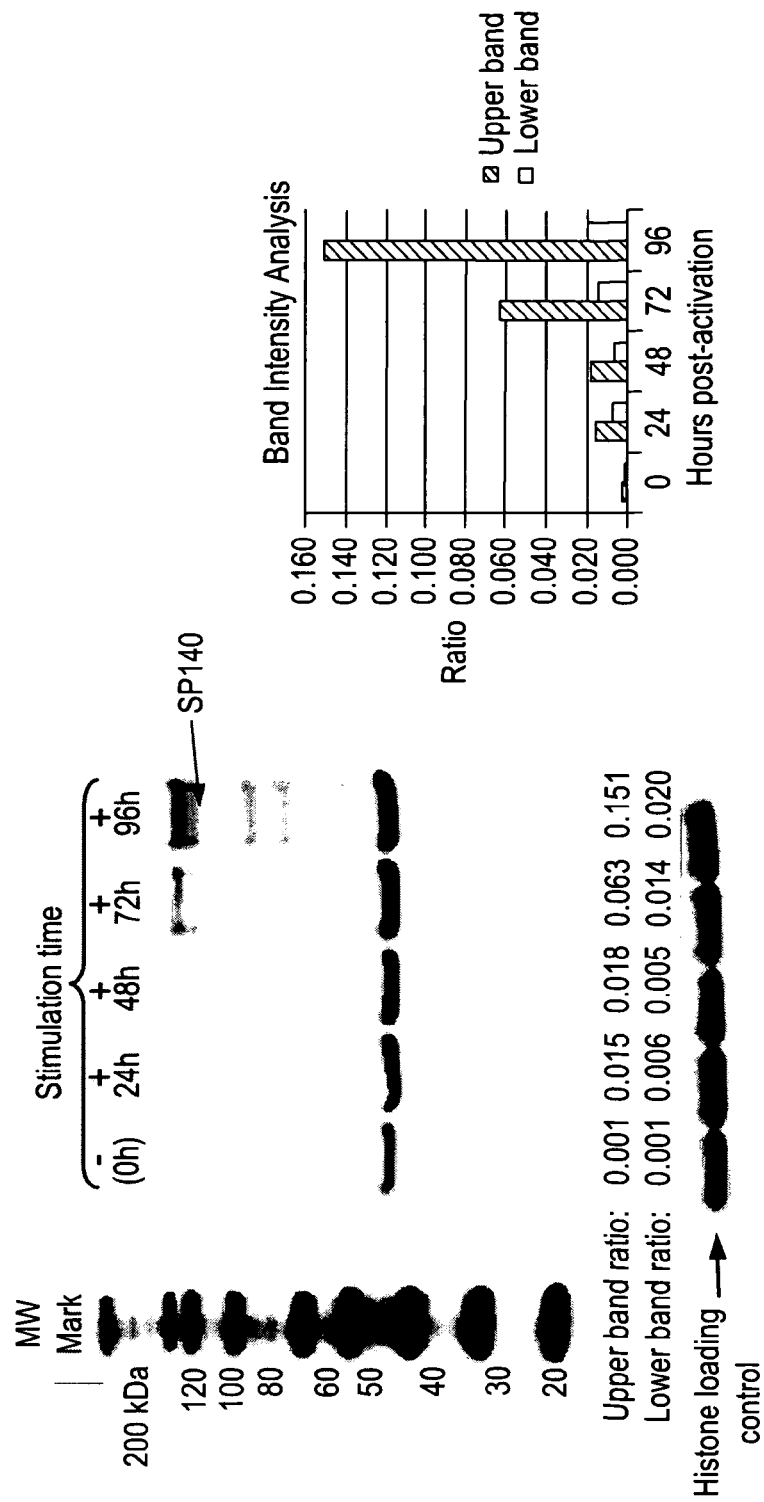
FIG. 8. SP140 expression in human CDC T cells. Purified CD4+T cells were activated with 0.1 mg/ml α-CD3 and 3 mg/ml α-CD28 for the indicated times. Western blots were probed with antibodies to SP140 or histone H3 as a loading control. Band intensity analysis was performed using QuantityOne software (Biorad), and the results are plotted as a ratio of the intensity of the SP140 bands to the intensity of the control H3 band. Ratios are plotted separately for the upper and lower SP140 bands.
Figure 9:
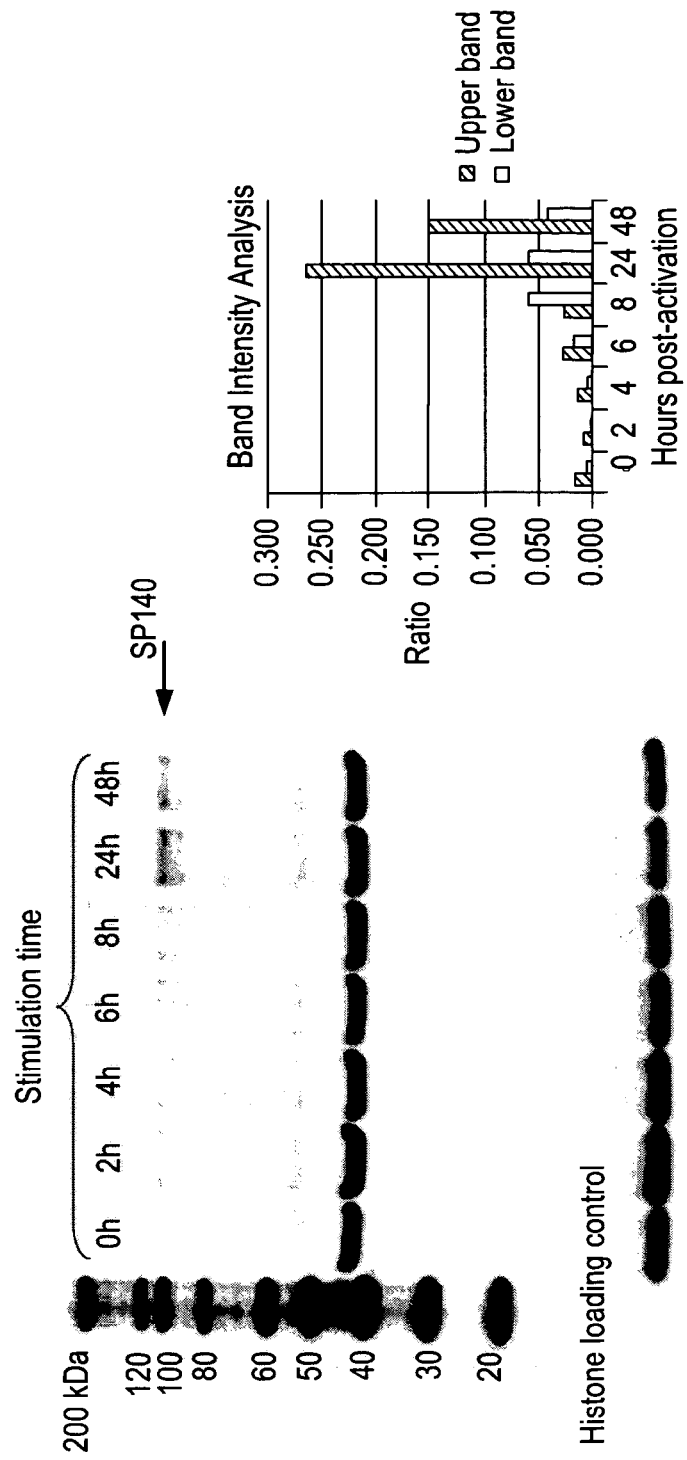
FIG. 9. SP140 expression in human monocyte-derived dendritic cells. CD14+ cells were isolated from PBMCs and differentiated to mdDCs using GM-CSF and IL-4 for 5 days. DCs were stimulated with 100 ng/ml LPS for the indicated times and total cell lysates were harvested, run on a 4-12% Bis-Tris gel and subjected to Western blotting. The membrane was probed with α-SP140 and α-H3 antibodies. Band intensity analysis was performed using QuantityOne software (Biorad) and results are plotted as a ratio of the intensity of the SP140 bands to the intensity of the H3 band. Ratios are plotted separately for the upper and lower SP140 bands.
Figure 10:
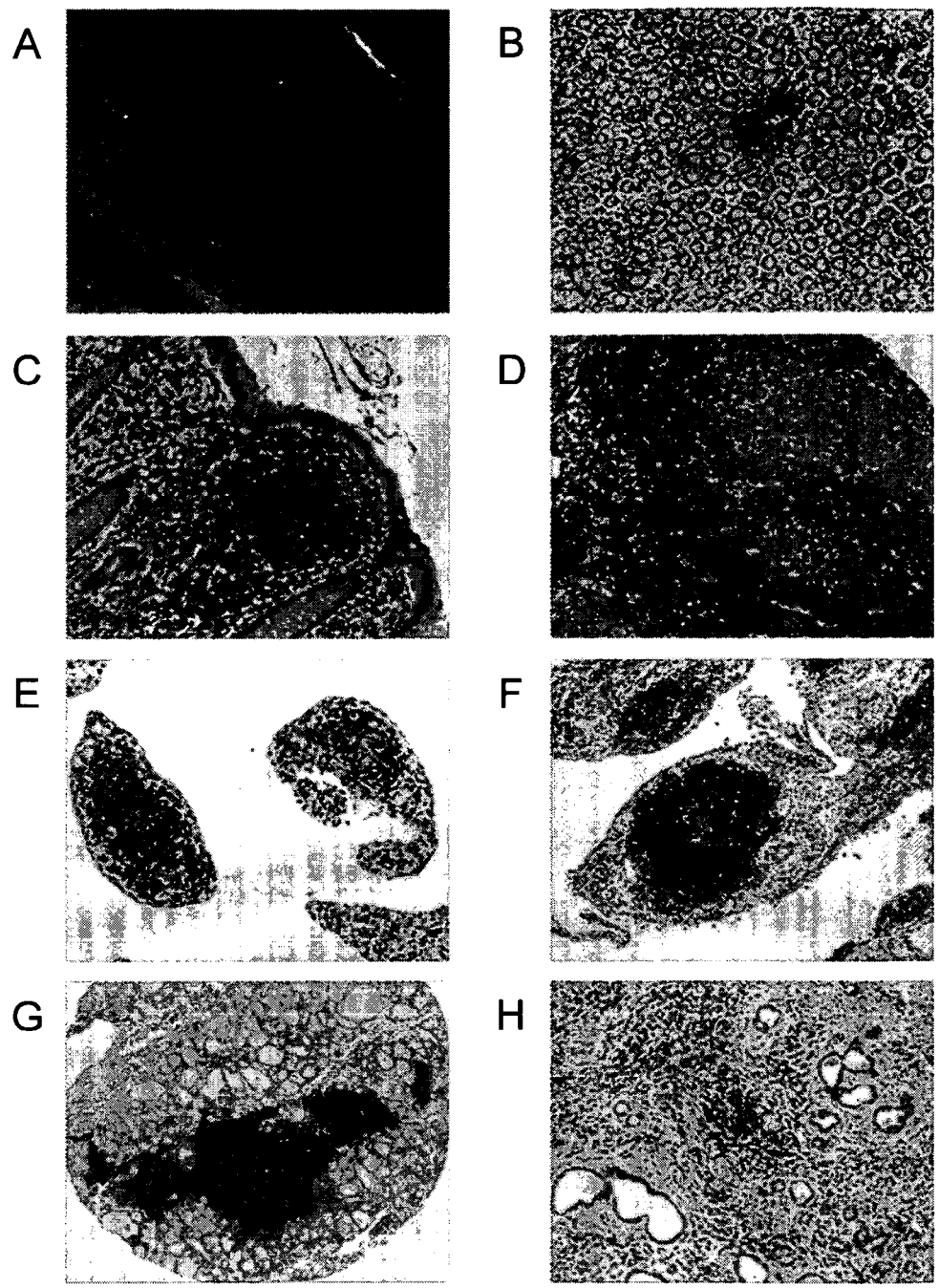
FIG. 10. Prominence of SP140+ cells in inflammatory infiltrates. Immunohistochemistry was used to assess SP140 protein expression in a variety of normal and inflamed tissues. (A) Tonsil tissue. The tonsil control shows positive cells in the germinal centre, in the mantle zone and in the interfollicular space, including populations of B and T cells. (B) Normal ileum. A small focus of SP140+ cells is apparent in the gut-associated lymphoid tissue. (C—H) Examples showing SP140+ mononuclear infiltrates in inflamed tissues: (C) appendicitis, appendix, (D) Crohn's disease, colon, (E) psoriatic arthritis, synovium, (F) rheumatoid arthritis, synovium, (G) Hashimoto's thyroiditis, thyroid, (H) Sjogren's syndrome, cervical cyst.

To investigate further the association between SP140 and immune inflammatory function, we assessed expression of SP140 protein under resting versus activated/inflamed conditions. To examine the regulation of SP140 expression in T cells, SP140 protein was measured by Western blotting, initially in monocyte-depleted, T cell enriched PBMCs before and after activation with anti-CD3/CD28 (FIG. 7). While SP140 protein was detected in resting cells, a strong increase in SP140 protein was observed after T cell stimulation (FIG. 7C). Assessment of SP140 protein expression in purified $CD4^+$ T cells at different times after stimulation with anti-CD3/CD28 confirmed that SP140 was indeed expressed in T cells and that T cell expression of SP140 increased after activation (FIG. 8). SP140 protein was elevated 24h after T cell stimulation and levels continued to increase at least until 96h post-activation. Similarly, we observed a marked increase in SP140 protein in DCs 24 hours after stimulation with LPS (FIG. 7D, 9). DC SP140 protein levels remained elevated at least until 48h after treatment with LPS (FIG. 9). Thus, elevated expression of SP140 protein is associated with T cell and DC activation. Additional evidence for up-regulation of SP140 under conditions of immune activation was provided by examining SP140 expression in human tissues by immunohistochemistry (FIG. 10). Assessment of expression in a variety of healthy and inflamed tissues revealed that SP140 protein was restricted to mononuclear cells. Hence, SP140 staining was observed in T and B cells in normal lymphoid tissues, but was largely absent from healthy non-lymphoid tissues (apart from normal lymphoid structures present in some tissues). Strikingly, large infiltrates of cells strongly staining for SP140 were observed in numerous inflamed tissues from a variety of autoimmune/inflammatory conditions. This included: Hashimoto's thyroiditis, thyroid; Crohn's disease colon; appendicitis, appendix; Sjogren's syndrome, cervical cyst; rheumatoid arthritis, synovium; psoriatic arthritis, synovium; Subacute granulomatous Thyroiditis, thyroid; Biliary Cirrhosis, liver; Sarcoidosis, lung; Ulcerative colitis, colon (FIG. 10 and data not shown). Thus, SP140 expression is increased in immune cells after activation and $SP140^+$ cells are prominent in inflamed tissues, further implicating this protein in inflammation and autoimmunity.

Finally, we explored the possibility that SP140 function is linked to its ability to bind chromatin, a key property of bromodomain-containing proteins. Hence, one way in which SP140 might function to control cytokine production would be by binding to chromatin within or near cytokine genes and regulating access of the gene to components of the transcriptional machinery. However, no information has been published regarding an association between SP140 and chromatin. To address this possibility, we conducted chromatin immunoprecipitation (ChIP) experiments to determine whether SP140 protein can associate with cytokine genes in DCs, and whether this is influenced by DC activation.

Figure 11:
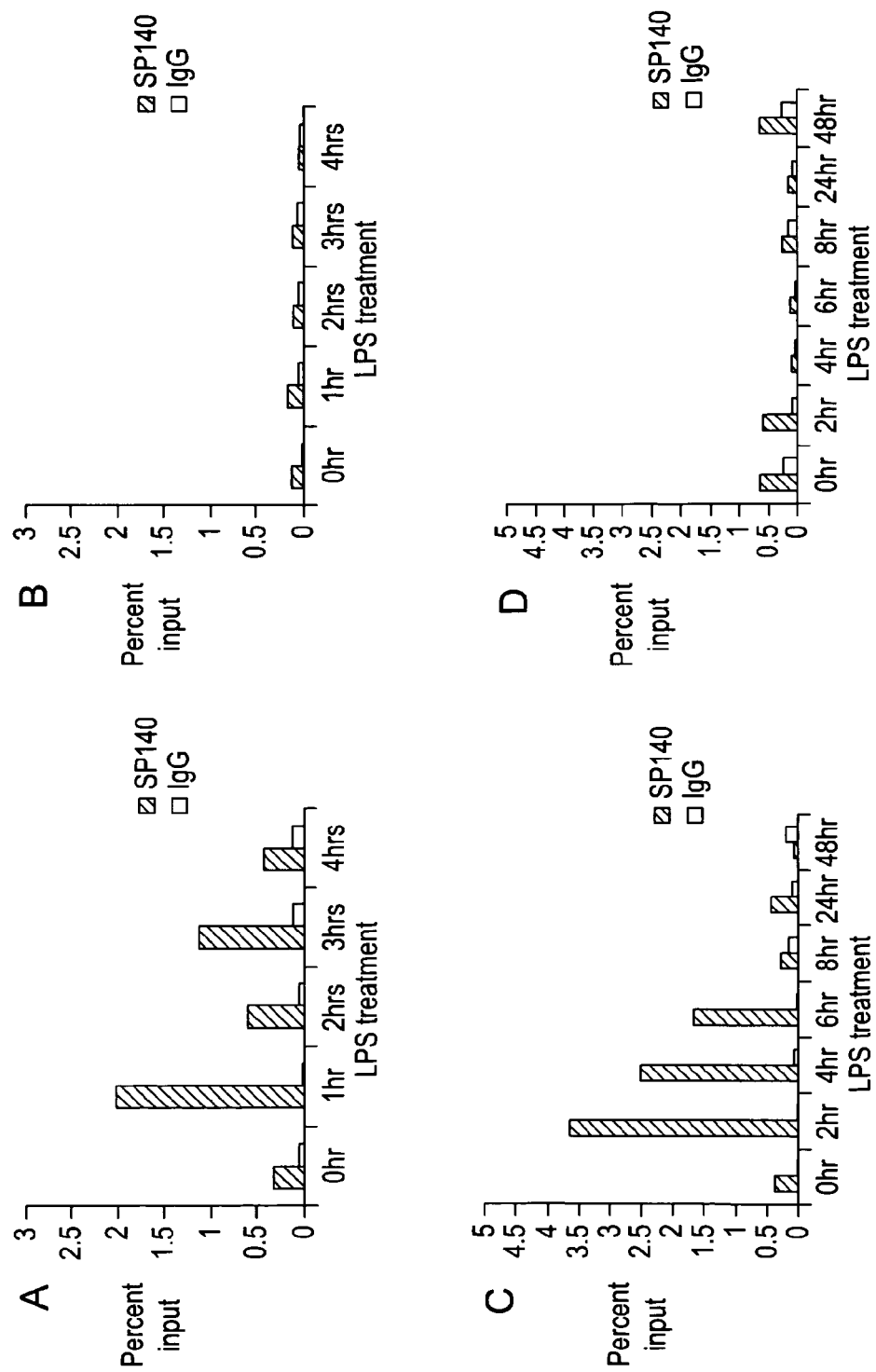
FIG. 11. SP140 associates with the transcription start site of TNF-α after dendritic cell activation. Data show results of 2 independent ChIP experiments using antibodies against SP140 or an IgG negative control antibody (IgG). ChIPs were conducted on dendritic cells at the indicated times after LPS stimulation. DNA enrichment in the ChIP samples was measured at (A, C) the TNF-α transcription start site (TSS) or (B, D) the human β-globin TSS. All results are plotted as the percent of input DNA.

ChIP was conducted in untreated DCs and DCs at several time points after treatment with LPS (FIG. 11). Compared to a negative control antibody, ChIP using anti-SP140 antibody showed enrichment of DNA at the TNF-α transcription start site (TSS) in resting DCs (FIG. 11A, C). This observation suggested that SP140 exhibits basal association with this cytokine gene locus in unactivated DCs. Notably, by one hour after treatment of DCs with LPS, SP140 showed strongly increased association with the TNF-α TSS (FIG. 11A), but not with the TSS of the β-globin gene, which is not expressed in DCs (FIG. 11B, D). The amount of SP140 associated with the TNF-α TSS returned to baseline by 8 hours after LPS treatment (FIG. 11C). These data provide the first evidence that SP140 can associate with chromatin, and are consistent with the idea that SP140 plays a role in regulating inflammatory cytokine expression through its ability to associate with chromatin at cytokine gene loci.

In summary, these data demonstrate an unexpected role for the bromodomain-containing protein SP140 in the inflammatory immune response. Inhibiting the expression and/or function of this protein represents a novel approach to the treatment of autoimmune and inflammatory diseases.

Methods:

Isolation of human PBMCs: (All preparation done at RT). Defibrinated human blood (25-30 ml/tube) was centrifuged at 2000 rpm for 10 min., after which the serum was removed and heat inactivated at 56° C. for 30 min. Tubes were filled to 50 ml with PBS (+Ca+Mg) and mixed thoroughly. 25 ml of diluted blood was layered over 15 ml of Lymphoprep and centrifuged at 2500 rpm for 20 min. at RT (brake off). Monolayers were transferred to clean labelled tubes (two monolayers pooled/tube). The tubes were filled to 50 ml with PBS and centrifuged for 10 min. at 2500 rpm.

Isolation of $CD4^+$ T cells: PBMCs were resuspended in 1 ml 2% FBS in PBS in 50 ml tube. Cells were counted and the volume of PBMC suspension adjusted to $1\times10^7$ cells/0.1 ml 2% FBS in PBS. 20 µl of antibody mix (Provided in kit) was added/$1\times10^7$ cells. Cells were incubated for 10 mins. @ 4° C. (in fridge). The volume in the tube was made up to 50 ml with 2% FBS in PBS, after which the tube was centrifuged for 5 mins. at 1600 rpm. Cells were resuspended in 0.9 ml 2% FBS in PBS/$10^7$ cells. 100 µl of washed Dynal beads was added/$10^7$ cells. Cells were mixed with beads at RT for 15 mins. Rosettes were resuspended by careful pipetting and the volume in the tube was increased by adding 1 ml 2% FBS in PBS/$10^7$ cells. The tube was then placed in a Dynal magnet for 2 minutes and supernatant transferred ($CD4^+$ T cells) to a fresh tube. Cells were centrifuged at 1600 rpm for 5 minutes in a benchtop Sorvall centrifuge. Cells were resuspended in 1 ml medium in an eppendorf tube and placed in an eppendorf magnet to remove any remaining contaminating Dynal beads. Cells were transferred to a clean eppendorf and the process repeated a second time. Cells were counted and resuspended in medium at $5\times10^8$ cells/ml. In some cases, memory/effector T cells were purified from total $CD4^+$ T cells using the Miltenyi T cell memory negative selection kit (Miltenyi Biotech Ltd) following the manufacturer's recommended protocol.

Preparation of monocyte-derived DCs: PBMC were resuspended at $10^8$ cells/ml in Miltenyi Buffer at 4° C. 100 µl of MACS CD14 Beads were added for every $10^8$ cells and and the mixture incubated on ice for 15 minutes. 10 × the volume of Miltenyi Buffer was added and the cells were pelleted by centrifugation. Cells were resuspended in 1 ml of Miltenyi Buffer/$10^8$ cells. 3 ml of Miltenyi Buffer was run through an LS column in place on the magnet, after which the cell suspension was added to the column. Once cells had entered the column, 3 ml of Miltenyi Buffer was added and this step was repeated two more times. LS columns were taken out of the Magnet and placed over 15 ml tubes. 5 ml of Miltenyi Buffer was added and cells were eluted using the syringe barrel as a plunger. Cells were pelleted by centrifugation and resuspended in 1 ml of medium for a cell count. The purified monocytes were resuspended at $10^6$ cells/ml in RPM! 1640/L-Glu /P/S/10% HI FBS +30 ng/ml GMCSF and 20 ng/ml IL-4 (R&D systems #204-IL).

DC activation: After 7 days culture in GMCSF and IL-4, cells were harvested into a 50 ml Falcon tube, centrifuged at 1600 rpm for 5 minutes, counted and resuspended at $1\times10^6$ cells/ml. Curdlan (WAKO cat number 034-09901) was added at 100 µg/ml, or LPS was added at 100 ng/ml and the DCs were cultured for 4 hours at 37° C./5%CO2. Cells were then centrifuged at 1600 rpm for 5 minutes and the supernatant discarded. Cells were washed once with IMDM medium (IMDM (Gibco)/10% heat inactivated autologous human serum/Penicillin/Streptomycin/L-Glutamine) and then resuspended in IMDM medium.

T cell transfection and activation: After overnight culture at 37° C./5%CO2, primary T cells were transfected with siRNAs by nucleofection (Amaxa T cell nucleofecter kit—DHPA-1002). siRNA reagents were pre-plated (2 µl of 20 µM solution) into a 96 well U'bottom plate such that a final concentration of 2 µM would be achieved. T cells were centrifuged at 1500 rpm for 10 minutes and all growth media removed. Nucleofecter buffer (plus supplement, made according to the manufacturer's protocol) was added to the cells such that each 20 µl contained 100,000 cells. Cells were added (20 µl) to the siRNA reagent in the U'bottom plates. 20 µl aliquots of cells/reagent were carefully added to each well of 96 well nucleofecter plates. The plates were placed into the Amaxa nucleofector and program EH-100 applied to all wells. After removal of the Amaxa plate, 100 µl of pre-warmed medium (IMDM/10% heat inactivated autologous serum/Penicillin/Streptomycin/L-Glutamine) plus 1 ng/ml IL-7 was added to each well. Cells were immediately removed from the Amaxa plate wells (100 µl per well recovered) and added to a second U'bottom plate containing an additional 100 µl pre-warmed media. Cells were cultured for a further 48 hours at 37° C. to allow knockdown to proceed. Subsequently, 160 µl medium was removed and 80 µl of fresh medium added. For T cell activation by DCs, 100 µl of the cell suspension was then transferred to a 96 well flat bottomed plate together with 100 µl of LPS- or curdlan-activated DCs per well. Culture supernatants were harvested 3-4 days later for cytokine analysis. For T cell activation by antibodies, cells were stimulated with 0.1 mg/ml α-CD3 and 3 mg/mla-CD28.

HuT78 cell transfection and activation: $10^6$ cells were suspended in 100 µl of Nucleofection buffer (Lonza, cat # VCA-1001) and 20 µl siRNA (20 µM) was added to the cell suspension. In addition to siRNAs targeting SP140, and siRNA versus IL-13 (Ambion, cat # AM16704) was used in these studies. Suspension containing cells and siRNAs were transferred to Amaxa cuvettes, placed in an Amaxa nucleofector and voltage (program V-001) was applied. 500 µl of medium (RPMI 1640, 10% FBS, 2 mM Glutamax, penicillin/streptomycin) was added after which the cell suspension was transferred to a 24 well plate and topped with another 500 µl of medium. The cells were incubated at 37° C. for 48 hours, harvested, pelleted and resuspended in 1 ml of medium. 12.5 µl of Human T-activator Dynabeads (Invitrogen, cat no. 11131 D_(50254642)) was added to each sample well. Cells were incubated for 24 hours, after which supernatants were removed for cytokine analysis.

Cytokine analysis: Cytokines were assayed using MSD plates and read in a MSD Sector 6000 plate reader.

Immunohistochemsitry: An anti-SP140 antibody produced in rabbit (HPA006162; Sigma Prestige Antibody) was used to visualise SP140 protein in a Cambridge Bioscience 69571061 Normal Human tissue microarray, a Cambridge Bioscience 4013301 Human Autoimmune Array, a Cambridge Bioscience 4013101 Human Colitis Array and on in house rheumatoid arthritis synovial samples. Anti-SP140 antibody was detected with a Leica polymer secondary antibody. Sections were de-waxed using proprietary ER1, low pH 6 and ER2, high pH 8 buffers for 20 minutes at ~98° C. Sites of antibody binding were visualised with peroxidase and DAB. Staining was performed on a Leica Bondmax immunostaining instrument, using protocol IHC F.

Western Blotting:

Whole cell lysates were prepared by resuspending cell pellets in a lysis and reducing buffer containing 100 µl DTT 1.5M, 275 µl $H_2O$ and 375 µl NuPAGE®LDS Sample Buffer (Invitrogen). SDS-PAGE Samples were heated for 5 min at 80-95° C. (thermobloc) and then sonicated for 1-5 seconds. Samples were were loaded on a NuPAGE® 4-12% Bis-Tris Gel (Invitrogen) and run for one hour at 100 mA/gel. Proteins were transferred to membranes by semi-dry transfer using the iBlot™ Gel Transfer Stacks Nitrocellulose Mini kits (Invitrogen). For detection, the nitrocellulose membrane was incubated with 10 mL of PBS containing 3% non-fat milk, pH 7.4 (Sigma) for 1-3 hours at room temperature with shaking, to block non specific sites. The primary antibody (anti-SP140 Prestige antibody, HPA006162, Sigma, used at 1:500) was added and the membrane was incubated overnight at 4° C. with shaking. The membrane was washed in mQ PBS-0.1% Tween 20 to eliminate excess primary antibody. The secondary antibody (anti-rabbit-IgG-HRP, Sigma) was added and the membrane was incubated for one hour at RT with shaking and washed in PBS-0.1%Tween 20 as described above. The image of the membrane was developed using Supersignal® West Femto Maximum Sensitivity Substrate kit (Thermo Scientific) or Femto solution (Pierce, Northumberland, UK) and captured using the LAS-3000 chemiluminescence imager (Fujifilm or Carestream). The antibodies were stripped off and the membrane was re-probed with an anti-histone H3 antibody (Abcam). Histone H3 served as loading control.

ChIP studies in DCs:

DCs were plated at a concentration of $1 \times 10^6$/ml in 4 ml in 6 well plates and incubated for 0, 2, 4, 6 or 24 hours with 100 ng/ml LPS. Cells were incubated at the same concentration without stimulation as a control. After incubation cells from one well treated with LPS and one unstimulated well were counted as representative of the plate. $5 \times 10^6$ cells were harvested for each condition. 400 µl fix solution was added to each well, mixed and the cells were incubated at 37° C. for 10 minutes. 125 mM glycine was added (200µl/well) to stop fixation and cells were incubated at RT for 5 minutes. The cells were harvested and washed twice with ice cold PBS centrifuging at 1,500rpm at 4° C. for 5 minutes after each wash. The cell pellet was snap frozen in liquid nitrogen and stored at -80° C. for four days. The cell pellets were defrosted on ice and resuspended in 100 µl of lysis buffer/IP, incubating on ice for 10 minutes with mixing every few minutes. The nuclei were sonicated using the bioruptor - sonicating for 30 minutes, 30 seconds on and 30 seconds off. Cell debris was removed by centrifugation (5 minutes at 1,500rpm) and the chromatin was transferred to a new tube.

2.4 ml Protein A/salmon sperm DNA beads were washed five times with PBS (+PIC) and two times with dilution buffer (+PIC), centrifuging at 2,000 rpm for 1 minute between washes. 25 µl chromatin was reserved as input and stored at -20° C. while the remainder was aliquoted into eppendorf tubes in 100 µl aliquots and diluted 1:10 with dilution buffer. 40 µl protein A/salmon sperm DNA beads was added to each eppendorf in order to pre-clear the chromatin and the chromatin was incubated with rotation at 4° C. for 3 hours. After incubation the chromatin was centrifuged at 2,000 rpm 1 minute and removed to a fresh tube. 5 µg antibody was added to the samples as follows:

| Antibody | Company | Lot and concn |
|---|---|---|
| Input | — | — |
| Rabbit IgG | Abcam ab37415 | 681902 5 mg/ml |
| α-SP140 | Abnova H00011626-MO7 | 08221-359 WULZ 1 mg/ml |

Chromatin was incubated with the antibody with rotation at 4° C. overnight. 80 µl pre-washed Protein A/salmon sperm DNA beads were added to each sample and the chromatin was incubated on a rotary mixer for 5 hours at 4° C. The samples were centrifuged at 2,000 rpm for 1 minute, the supernatant removed and the beads washed in the following wash buffers for 5 minutes with rotation at RT:Low salt buffer ×1, High salt buffer ×1, LiCl buffer ×1, TE ×2.

After the final wash, the beads were resuspended in 100 µl elution buffer and incubated at RT with rotation for 10 minutes. The eluted chromatin was removed to a fresh tube and the beads incubated with a further 100 µl elution buffer. The two eluates were combined and incubated with 8 µl 5M NaCl at 65° C. overnight. The samples were incubated with 0.2 µl 20 mg/ml RNaseA for 1 hour at 37° C. and then with 4 µl 0.5M EDTA, 8 µl 1M Tris-HCl pH6.5 and 0.4 µl 20 mg/ml Proteinase K for 1 hour at 45° C. The DNA was purified using the Zymo ChIP DNA Clean & Concentrator Kit for Taqman. Following manufacturer's instructions, 1 ml DNA Binding buffer was added to each sample, mixed and the samples were loaded onto the columns. For the samples immunoprecipitated with H3 50% of the sample was loaded onto the columns. The columns were washed twice with 200 µl DNA Wash Buffer and DNA eluted with 100 µl of Elution Buffer.

DNA was amplified using Sybr Green and primers against TNFα TSS and 5' human β-globin (primers from Invitrogen).

SEQID: 8 TNFαF (TSS_TNFaF) GGGACATATAAAGGCAGTTGTTGG

SEQID: 9 TNFα R (TSS_TNFaR) TCCCTCTTAGCTGGTCCTCTGC

SEQID: 10 Human β-globin F (5C_HBBF) AACAGCCAAGTCAAATCTGC

SEQID: 11 Human β-globin R (5C_HBBR) GGCACACGTGTATCCCTGAG

PCRs were performed in 10 µl volume with 4 µl DNA, 5 µl sybr green mix and 0.1 µl 25 mM forward primer and 0.1 µl 25 mM reverse primer. PCRs were run in triplicate on Applied Biosystems 9700HT, using the following programme: 50° C. 2 minutes, 95° C. 10 minutes and 40 cycles of 95° C. 15 seconds, 60° C. 1 minute. Human genomic DNA standards $1-1 \times 10^5$ copies were used to obtain the standard curve. The quantity of DNA obtained following amplification was determined by the Applied Biosystems SDS software from the standard curve. The quantity was averaged from the triplicates and expressed as percent of input. N. B. Any obvious outliers occurring due to pipetting errors, particularly noticeable when there are low levels of template, were not included in the calculations.

Reagents and Solutions

| Reagent | Source Order details |
|---|---|

Materials:
Miltenyi Buffer: PBS w/o Ca and Mg, 0.5% BSA, 5 mM EDTA Miltenyi (MACS) CD14 Beads: CD14 MicroBeads, human 2 ml, contains 0.1% BSA, 0.05% Azide (in cold room).

BSA: Albumin, Bovine Fraction V Powder (Sigma, A-1933)

EDTA: Ethylenediaminetetraacetic acid (Sigma, E-7889). Stock conc- 0.5M
siRNAs: All siRNAs were obtained from Qiagen.
NuPage 4× SDS sample buffer (Invitrogen, NP0007)
DTT 1,4 dithiothreitol (Roche, 10708984001)
NuPage antioxidant (Invitrogen, NP0005)
NuPage MES SDS running buffer (Invitrogen, NP0002)
NuPage 4-12% Bis Tris Gel 1.5 mm 15 well (Invitrogen, NP0336BOX)
iBlot gel transfer stacks nitrocellulose (Invitrogen, 1B3010-01)
Seeblue Plan2 prestained standard (Invitrogen, LC5925)
PBS+3% non-fat milk (Sigma, P2194)
Novex colloidal blue staining kit (Invitrogen, LC6025)
Super signal West femto kit (Thermo Scientific, 34096)
IgG elution buffer (Thermo Scientific, 21004)
Gel dry drying solution (Invitrogen, LC4025)
DMEM (Invitrogen, 32430027)
Protein A / ss DNA beads (Fisher Scientific, MZ16157)
Protease Inhibitor Cocktail (Roche Diagnostics, 11836170001)
Formaldehyde soin (Sigma, F1635)
EDTA (Sigma, E-7889)
NaCl (Sigma, S5886)
Tris-HCl pH8 (Sigma, T3038)
Triton x-100 (Sigma, x-100)
NP-40 (Fluka, 74385)
SDS (Sigma, L4509)
Lithium Chloride (Sigma, L7026)
Sodium deoxycholate (Sigma, D6750)
Proteinase K (20 mg/ml) (Invitrogen, AM2548)
Zymo ChIP DNA clean kit (Cambridge Bioscience, D5201)
Optical 384 well plates (Invitrogen, 4326270)
Optical adhesive film (Invitrogen, 4311971)
Sybr Green master mix (Invitrogen, 4364344)
Proteinase K (20 mg/ml) (Invitrogen, AM2548)
Zymo ChIP DNA clean kit (Cambridge Bioscience, D5201)
Optical 384 well plates (Invitrogen, 4326270)

Fix solution: 10% formaldehyde, 0.1M NaCl, 1 mM EDTA, 0.5 mM EGTA, 10 mM Iris-HCl pH8
Lysis Buffer: 1% SDS, 10 mM EDTA, 50 mM Tris-HCl pH 8
Dilution Buffer: 0.01% SDS, 1.1% Triton X-100, 1.2 mM EDTA, 16.7 mM Tris-HCl pH8, 167 mM NaCl
Low salt buffer: 0.1% SDS, 1% Triton X-100, 2 mM EDTA, 150 mM NaCl, 20 mM Tris-HCl pH 8
High salt buffer: 0.1% SDS, 1% Triton X-100, 2 mM EDTA, 500 mM NaCl, 20 mM Tris-HCl pH 8
Lithium chloride wash buffer: 0.25M LiCl, 1% NP40, 1% Na Deoxycholate, 1 mM EDTA, 10 mM Tris-HCl pH8
TE: 10 mM Tris-HCl pH8, 1 mM EDTA
Elution buffer: 1% SDS, 100 mM NaHCO3

REFERENCES (1) Struhl K. Histone acetylation and transcriptional regulatory mechanisms. Genes Dev. 1998 Mar. 1; 12(5):599-606.
(2) Jeanmougin F, Wurtz JM, Le Douarin B, Chambon P, Losson R. The bromodomain revisited. Trends Biochem Sci. 1997 May; 22(5):151-3.
(3) Tamkun J W, Deuring R, Scott M P, Kissinger M, Pattatucci A M, Kaufman T C, Kennison J A. Brahma: a regulator of Drosophila homeotic genes structurally related to the yeast transcriptional activator SNF2/SWI2. Cell. 1992 Feb. 7; 68(3):561-72.
(4) Wolters N M, MacKeigan J P. From sequence to function: using RNAi to elucidate mechanisms of human disease. Cell Death Differ. 2008 May;15(5):809-19.
(5) Miossec P, Korn T, Kuchroo V K. Interleukin-17 and type 17 helper T cells. N Engi J Med. 2009 Aug. 27;361(9):888-98.
(6) Dardalhon V, Korn T, Kuchroo V K, Anderson A C. Role of Th1 and Th17 cells in organ-specific autoimmunity. J Autoimmun. 2008 November;31(3):252-6.
(7) Kleinschek M A, Boniface K, Sadekova S, Grein J, Murphy E E, Turner S P, Raskin L, Desai B, Faubion W A, de Waal Malefyt R, Pierce R H, McClanahan T, Kastelein R A. Circulating and gut-resident human Th17 cells express CD161 and promote intestinal inflammation. J Exp Med. 2009 Mar. 16; 206(3):525-34.

What is claimed is:

1. A method of treating autoimmune and inflammatory diseases or conditions in a mammal, which comprises the administration of a therapeutically effective amount of an inhibitor of the bromodomain-containing protein SP140.

2. The method of claim 1 wherein said mammal is a human.

* * * * *